(12) United States Patent
Koschitzky

(10) Patent No.: US 7,125,579 B2
(45) Date of Patent: Oct. 24, 2006

(54) ALGAE-RESISTANT ROOFING MATERIAL AND METHODS

(76) Inventor: Henry Koschitzky, 57 York Downs Drive, Downsview, Ontario (CA) M3H 1H7

( * ) Notice: Subject to any disclaimer, the term of this patent is extended or adjusted under 35 U.S.C. 154(b) by 413 days.

(21) Appl. No.: 10/737,768

(22) Filed: Dec. 18, 2003

(65) Prior Publication Data

US 2005/0136216 A1 Jun. 23, 2005

(51) Int. Cl.
*B05D 1/12* (2006.01)
(52) U.S. Cl. ........................... 427/186; 427/188
(58) Field of Classification Search ............... 427/186, 427/188
See application file for complete search history.

(56) References Cited

U.S. PATENT DOCUMENTS 4,092,441 A * 5/1978 Meyer et al. ............... 427/453
5,356,664 A * 10/1994 Narayan et al. ........... 427/186

* cited by examiner

*Primary Examiner*—Fred J. Parker
(74) *Attorney, Agent, or Firm*—Bereskin & Parr

(57) ABSTRACT

A method of making algae-resistant shingles in which the algae-inhibiting material, usually a copper compound, is applied only to larger granules, instead of being applied to a full size range of granules. Use of the larger granules only, as algae-resistant granules, significantly increases the percentage of surface area of algae-resistant granules for releasing algae-inhibiting material and also reduces the material consumption of the algae-inhibiting material during production of the algae-resistant granules, thus substantially reducing cost.

5 Claims, 2 Drawing Sheets

ALGAE-RESISTANT ROOFING MATERIAL AND METHODS

FIELD OF THE INVENTION

This invention relates to an algae-resistant roofing material, such as a shingle, and to a method of producing the same. It also relates to granules used in algae-resistant roofing materials. The invention will be described with reference to a shingle.

BACKGROUND OF THE INVENTION

Algae-resistant shingles have been used for many years and have employed various algae-inhibiting substances to deter the growth of algae on the shingles. A widely used algae-inhibiting substance is copper, and algae-resistant shingles using copper-containing granules are shown and described, for example, in U.S. Pat. No. 5,356,664 to Narayan et al. In that patent, a blend of copper-containing algae-resistant granules and non-algae-resistant granules is used to produce the algae-resistant shingle, with the ratio of copper-containing algae-resistant granules to the non-algae-resistant granules being suggested as 1:9 by weight.

In the Narayan et al. patent, the copper-containing granules comprise a conventional substrate (usually crushed stone) having at least one inner ceramic coating which includes cuprous oxide, and a seal coating which regulates the leach rate of copper ions from the inner ceramic coating. The copper-containing granules leach copper ions during the service life of the algae-resistant shingle to inhibit algae growth on the shingle surface even when the shingle surface is exposed to substantial moisture.

While algae-resistant shingles using copper-containing granules have been well known for many years, they are costly due to the additional cost of the copper-containing granules. As compared with normal ceramic-coated colored granules, copper-containing granules require at least one additional inner ceramic coating comprising cuprous oxide and contain a significant amount of copper-containing raw material. In addition, much of the copper is wasted, since not all of the copper ions are available to be leached from the copper-containing granules. Only the copper ions in the portions of the copper-containing granules exposed to the environment can be leached out onto the shingle surface. The copper ions located in those portions of the copper-containing granules, which are embedded into the asphalt coating of the shingle, are not available to be leached out of the granules, since they are covered by asphalt.

BRIEF SUMMARY OF THE INVENTION

It is therefore an object of the invention to provide an algae-resistant roofing material, and a method of making the same, so as to provide improved availability for release from the granules of algae-inhibiting ions, while at the same time reducing the amount of algae-inhibiting substance needed in the algae-resistant granules, thus reducing cost.

In one aspect the invention provides a method of making algae-resistant roofing material comprising: (a) coating a substrate with an asphalt-based coating material; (b) selecting algae-resistant granules and non-algae-resistant granules; (c) said non-algae-resistant granules having nominal diameters between approximately 2 mm and 0.3 mm; (d) said algae inhibiting granules being primarily of sizes having nominal diameters between approximately 1 and 2 mm and not of other sizes; and (e) applying said algae-resistant granules and non-algae-resistant granules onto said coating material.

In another aspect the invention provides an algae-resistant roofing material comprising (a) a substrate; (b) a coating material on said substrate; (c) a plurality of granules embedded in said coating material; (d) said granules being a mixture of algae-resistant granules and non-algae-resistant granules; (e) said non-algae-resistant granules having a plurality of sizes within a normal size range, said sizes ranging from large sizes to small sizes; and (e said algae-resistant granules being primarily of said large sizes and not of other sizes.

In yet another aspect the invention provides a method for making a mixture of granules for use in a roofing material comprising: (a) selecting non-algae-resistant first granules having a nominal diameters between approximately 2 mm and 0.3 mm: (b) selecting as second granules some of said first granules, the nominal diameters of said second granules being between approximately 1 and 2 mm; (c) treating said second granules with an algae-inhibiting material to form algae-resistant granules; (d) mixing said algae-resistant granules and non-algae-resistant granules together in a selected ratio to form a granule blend, so that the algae-resistant granules in said blend consist primarily of said second granules in said blend, whereby to increase the effective exposed area of algae-resistant granules when said blend is applied to a roofing material while reducing the amount of said algae-inhibiting material in said granule blend.

Further objects and advantages of the invention will appear from the following description, taken together with the accompanying drawings.

DETAILED DESCRIPTION OF THE PREFERRED EMBODIMENT

Figure 1:
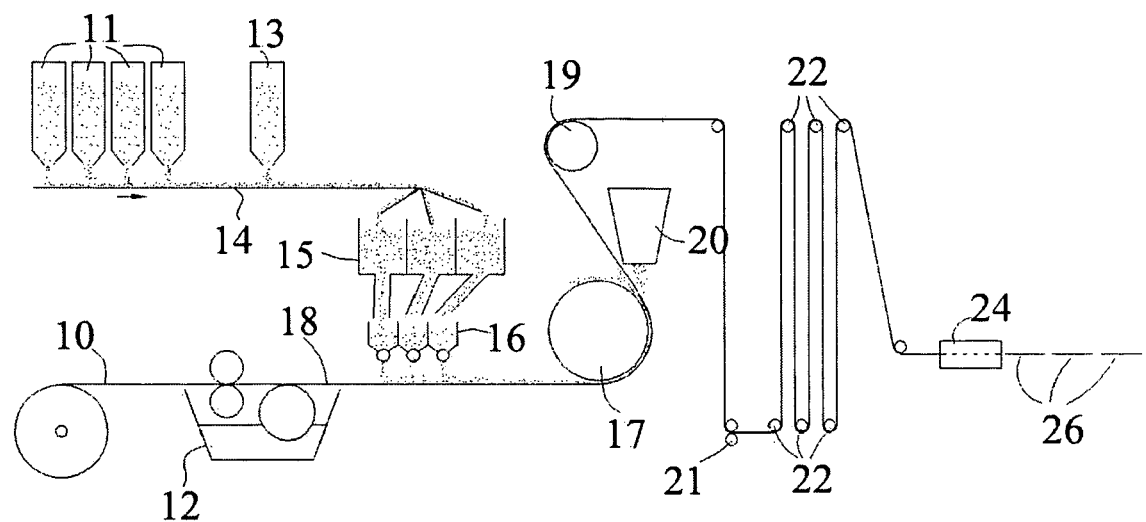
FIG. 1 is diagrammatic view showing a conventional method of producing asphalt-coated shingles.

The manufacture of conventional asphalt roofing shingles has been well known for many years. In the conventional method, as shown in FIG. 1, a strip 10 of base material (either felt or glass fiber) is unwound and is passed through a mineral-stabilized coating asphalt shown at 12, to coat the top and bottom surfaces of the strip 10. (If the strip 10 is felt, it is first saturated with asphalt in a separate bath, not shown.)

Normal non-algae-resistant granules indicated at storage silos 11 and algae-resistant granules indicated at storage silo 13, are fed onto belt conveyor 14 and conveyed to granule blending bins 15. Since the non-algae-resistant granules and algae-resistant granules stack on each other on belt conveyor 14, they are mixed when they are dropped into granule blending bins 15. The mixture of granules from bins 15 is directed to a blender 16. From blender 16, the blended granules are dropped and embedded into the hot top asphalt coating 18 to a certain distance. As is well known, the granules (typically crushed stone such as Andesite, commonly known as trap rock) serve to protect the asphalt coating from ultraviolet degradation and also decorate the resultant shingle.

The strip 10 then goes around the slate drum 17 and the granules are pressed further into the top asphalt coating 18 by the sheet tension. The strip 10 then passes under another hopper 20 where its bottom surface is coated with a non-stick material such as talc to prevent it from sticking to the machine and to other shingles when packaged.

The strip 10 then goes around the talc drum 19 where the excess granules on the top surface of the coating 18 are dumped off.

The strip 10 then passes through a press roll 21 that smoothes out the granules to a level surface and a series of rollers 22 where it is cooled.

The strip 10 is then slit and crosscut by a slitter and crosscutter 24 into a number of lanes of product shingles 26. The process shown has been somewhat simplified but is entirely conventional and well known.

Figure 2:
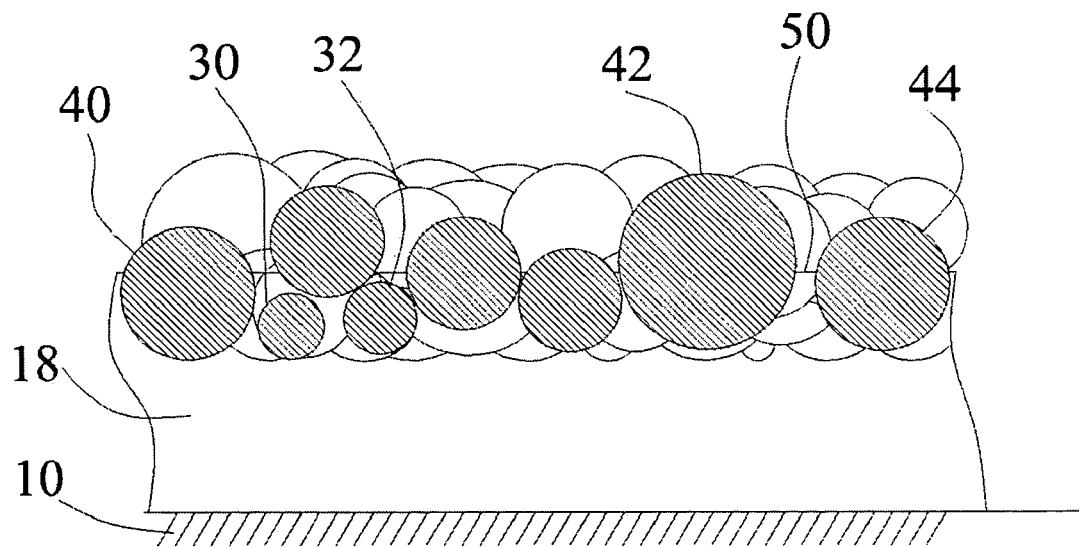
FIG. 2 is a schematic diagram showing granules with various sizes embedded into the top asphalt coating of a shingle made according to FIG. 1.

Reference is next made to FIG. 2, which shows various size granules 30, 32, 40, 42, 44 embedded in the top asphalt coating 18 on the top of the strip 10. It will be realized that the granule shape is not a perfect sphere. However for purposes of explanation, the granules are drawn as spheres in FIG. 2. The top surface of coating 18 is indicated at 50.

In FIG. 2, the granules are pressed into the top asphalt coating 18 to a certain depth as discussed above. The algae-inhibiting material in the portion of the algae-resistant granule surface which projects above the top surface 50 of coating 18 is available to be leached out onto the shingle surface to deter algae growth. On the other hand, the algae-inhibiting material in the portion of the algae-resistant granule surface under the coating surface 50 is not available to be leached out onto the shingle surface because it, is covered by asphalt and is not exposed to substantial moisture. This algae-inhibiting material under the coating surface 50 is wasted. Smaller granules, like these indicated at 30, 32, are more likely to be totally buried in the top asphalt coating 18 while larger granules, like 40, 42, 44, have a higher percentage of surface area exposed to the environment. Therefore, the algae-resistant granules with larger sizes are more effective to leach algae-inhibiting material than those with smaller sizes.

In the traditional method, the granules having a full normal size range are treated with the algae-inhibiting material. Since smaller granules are more likely to be totally buried in the top asphalt coating, the expensive algae-inhibiting material applied to the smaller granules is wasted. This invention selects only larger granules to be treated with the algae-inhibiting material. It therefore avoids the wastage of the algae-inhibiting material due to the smaller granules being totally buried in the coating, increases the percentage of the granule surface area bearing algae-resistant material exposed to the environment, and thus increases the effectiveness of leaching algae-inhibiting material onto the shingle surface. Since the effectiveness is increased, less granule surface in the blend requires to be coated with algae-inhibiting material and consequently, less algae-inhibiting material is required to achieve the same algae-inhibiting effect.

Referring to Table 1 below, the typical full size range, which are commonly used for producing copper containing granules for algae-inhibiting purposes (as shown in the Narayan et al. patent referred to above) and which are also commonly used in making standard non-algae-resistant shingles, is approximately from 0.3 mm to 2 mm in diameter.

| Nominal Diameter of Granules for Use in Producing Shingles, (mm) | % by Weight of Granules |
|---|---|
| 2 | 10% |
| 1.5 | 35% |
| 1 | 30% |
| 0.75 | 19% |
| 0.5 | 5% |
| 0.3 | 1% |
| Total | 100% |

In the Narayan et al. patent, the suggested ratio of algae-resistant to non-algae-resistant granules is 1:9 by weight (i.e. 10% algae-resistant granules). If the granules are embedded into the top coating to, for example, 1 mm depth, the smaller granules with nominal diameter below 1 mm are most likely to be totally buried in the top asphalt coating and cannot leach out algae-inhibiting material. Referring to Table 1 above, 25% of the granules have nominal diameter below 1 mm while 75% of the granules have nominal diameter equal or above 1 mm. This invention suggests using only larger algae-resistance granules, e.g. those having nominal diameters between 1 and 2 mm (the first three entries in the above Table). By eliminating the smaller algae-resistant granules (e.g. granules having nominal diameters shown in the last three entries in the Table), the total usage of the algae-resistant granules (in terms of percent by weight of the algae-resistant granules in the mixture) can be reduced by 25%. In other words, the percent by weight of algae-resistant granules in the mixture can be reduced from 10% by weight to a new value of 7.5% by weight, while the algae-resistant capability remains unchanged. Since the smaller granules are not required, the expensive algae-inhibiting material for the smaller granules can be saved.

The foregoing description has described a selection process for granules used to produce the algae-resistant granules used in manufacture of the shingles, and has discussed using larger rather than smaller granules as the algae-resistant granules. It will be realized that these algae-resistant granules are of course mixed with non-algae-resistant granules in the manufacture of the shingles. The overall process is simplified for illustration purposes and shown in FIG. 3.

Figure 3:
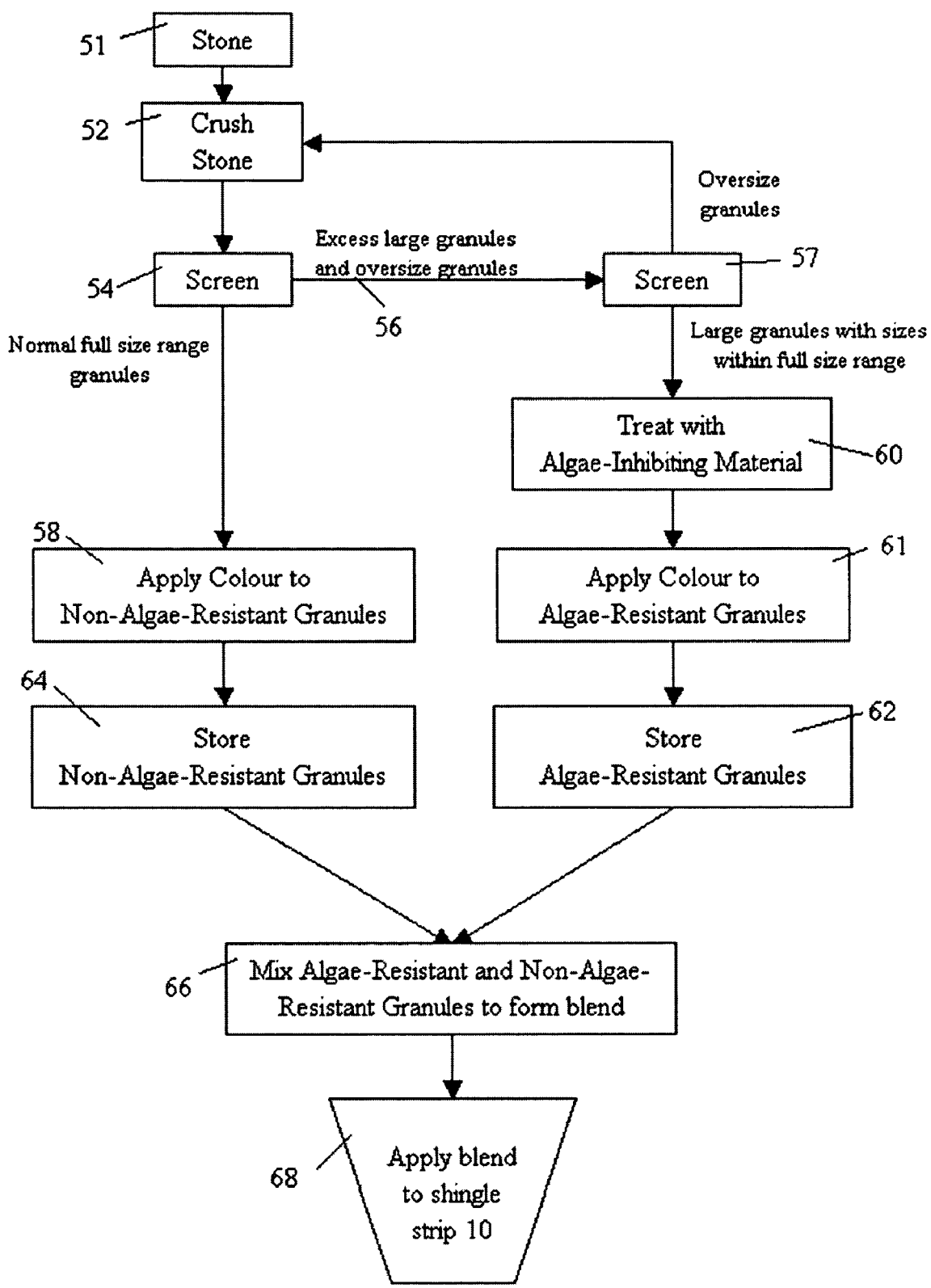
FIG. 3 is a diagrammatic view, largely in flow chart form, showing production of a blend of algae-resistant granules and non-algae-resistant granules for use in producing shingles according to the invention.

In the FIG. 3 process, suitable stone (such as trap rock) is selected at step 51 and is crushed at step 52. After the crushing step, the crushed stone is then screened at step 54. Normal granules having the desired full size range go through the screen at step 54 and are colored at step 58 and stored at 64. The excess large granules and oversize granules are removed at 56 and are further screened at step 57. The oversize granules return to step 52 for further crushing. The large granules having sizes within the desired full size range go through the screen at step 57 and are treated with algae-inhibiting material at step 60 and colored at step 61, in the conventional manner disclosed in the Narayan et al. patent. The disclosure of that patent and the references referred to therein are incorporated by reference into this disclosure.

The colored algae-resistant granules are stored at 62, while a set of ordinary colored granules not treated with algae-inhibiting material is stored at 64. The untreated granules stored at 64 would normally be of various sizes, i.e. they will have a complete spectrum of sizes. The colored algae-resistant granules are primarily large size granules of the complete spectrum. However, it will be realized that screening processes are never perfect, and therefore some small granules, smaller than the screen openings, may be retained in the screen at step 54. These smaller granules will also be coated with the copper-containing substance, and this will reduce slightly the increase in the effective exposed surface area of the copper-containing granules and the material saving of the copper-containing ceramic coating. This undesirable effect will normally be small.

After the blend 66 has been formed by suitable mixing, it is applied to shingles at step 68, as shown in FIG. 1.

While the foregoing disclosure has referred to the algae-inhibiting material as being a copper material, it will be realized that other algae-inhibiting materials or algaecides are known (for example zinc-containing materials) and may be used. The specific nature of the algae-inhibiting substance used does not form part of the present invention and all effective algae-inhibiting materials may be used in accordance with the invention.

In addition, while the description has referred to the manufacture of shingles, it will be realized that the invention is also applicable to sheet roofing of the kind which employs granules embedded in a coating. The coating need not be asphalt, but can be any other appropriate coating material as used in roofing.

Various other modifications and changes will become apparent to those skilled in the art, and it should be understood that this invention is not to be limited to the specific preferred embodiments which have been described.

I claim:

1. A method of making algae-resistant roofing material comprising:
   (a) coating a substrate with an asphalt-based coating material;
   (b) selecting algae-resistant granules and non-algae-resistant granules;
   (c) said non-algae-resistant granules having nominal diameters between approximately 2 mm and 0.3 mm;
   (d) said algae-resistant granules being primarily of sizes having nominal diameters between approximately 1 and 2 mm and not of other sizes; and
   (e) applying said algae-resistant granules and non-algae-resistant granules onto said coating material.

2. A method according to claim 1 wherein said algae-resistant granules includes copper.

3. A method according to claim 1 wherein said roofing material is a shingle.

4. A method of making a mixture of granules for use in a roofing material comprising:
   (a) selecting non-algae-resistant first granules having nominal diameters between approximately 2 mm and 0.3 mm;
   (b) selecting as second granules some of said first granules, the nominal diameters of said second granules being between approximately 1 and 2 mm;
   (c) treating said second granules with an algae-inhibiting material to form algae-resistant granules;
   (d) mixing said algae-resistant granules and non-algae-resistant granules together in a selected ratio to form a granule blend;

so that the algae-resistant granules in said blend consist primarily of said second granules in said blend, whereby to increase the effective exposed area of algae-resistant granules when said blend is applied to a roofing material while reducing the amount of said algae-inhibiting material in said granule blend.

5. A method according to claim 4 wherein said algae-inhibiting material includes copper.

* * * * *